(12) United States Patent
Künnecke

(10) Patent No.: US 6,544,393 B1
(45) Date of Patent: Apr. 8, 2003

(54) FLOW ANALYSIS CELL AND LAYERED SENSOR PERTAINING THERETO

(75) Inventor: Wolfgang Künnecke, Braunschweig (DE)

(73) Assignee: Trace Biotech AG, Braunschweig (DE)

(*) Notice: Subject to any disclaimer, the term of this patent is extended or adjusted under 35 U.S.C. 154(b) by 0 days.

(21) Appl. No.: 09/600,142

(22) PCT Filed: Jan. 14, 1999

(86) PCT No.: PCT/DE99/00063
§ 371 (c)(1),
(2), (4) Date: Aug. 31, 2000

(87) PCT Pub. No.: WO99/36786
PCT Pub. Date: Jul. 22, 1999

(30) Foreign Application Priority Data

Jan. 16, 1998 (DE) .......................... 198 01 344

(51) Int. Cl.⁷ .................. G01N 27/403; G01N 27/327; G01N 27/414
(52) U.S. Cl. .................. 204/409; 204/416; 204/403.01; 204/403.14; 422/82.01
(58) Field of Search ...................... 204/403.01, 403.14, 204/409, 416, 433; 422/82.01, 82.03, 82.02, 82.05

(56) References Cited

U.S. PATENT DOCUMENTS 5,211,830 A * 5/1993 Tomita et al. ............... 204/416
6,084,392 A * 7/2000 Shine et al. ................. 204/409
6,287,438 B1 * 9/2001 Knoll ..................... 204/403.13

FOREIGN PATENT DOCUMENTS

WO          9727475       *   7/1997

* cited by examiner

Primary Examiner—T. Tung
Assistant Examiner—Alex Noguerola
(74) Attorney, Agent, or Firm—Whitham, Curtis & Christofferson, PC

(57) ABSTRACT

The analysis flow cell provided with a thin-film or thick-film sensor is designed so that the input and outlet for the fluid to be investigated are on opposite sides of the sensor layer and so that there is at least one passage (24) transverse to the sensor film, which can be in the sensor film or beside it in a layer of carrier. The sensor can be a biosensor, in which a thin layer of platinum, gold, or graphite is coated with a biosensor material.

16 Claims, 6 Drawing Sheets

FLOW ANALYSIS CELL AND LAYERED SENSOR PERTAINING THERETO

Figure 1:
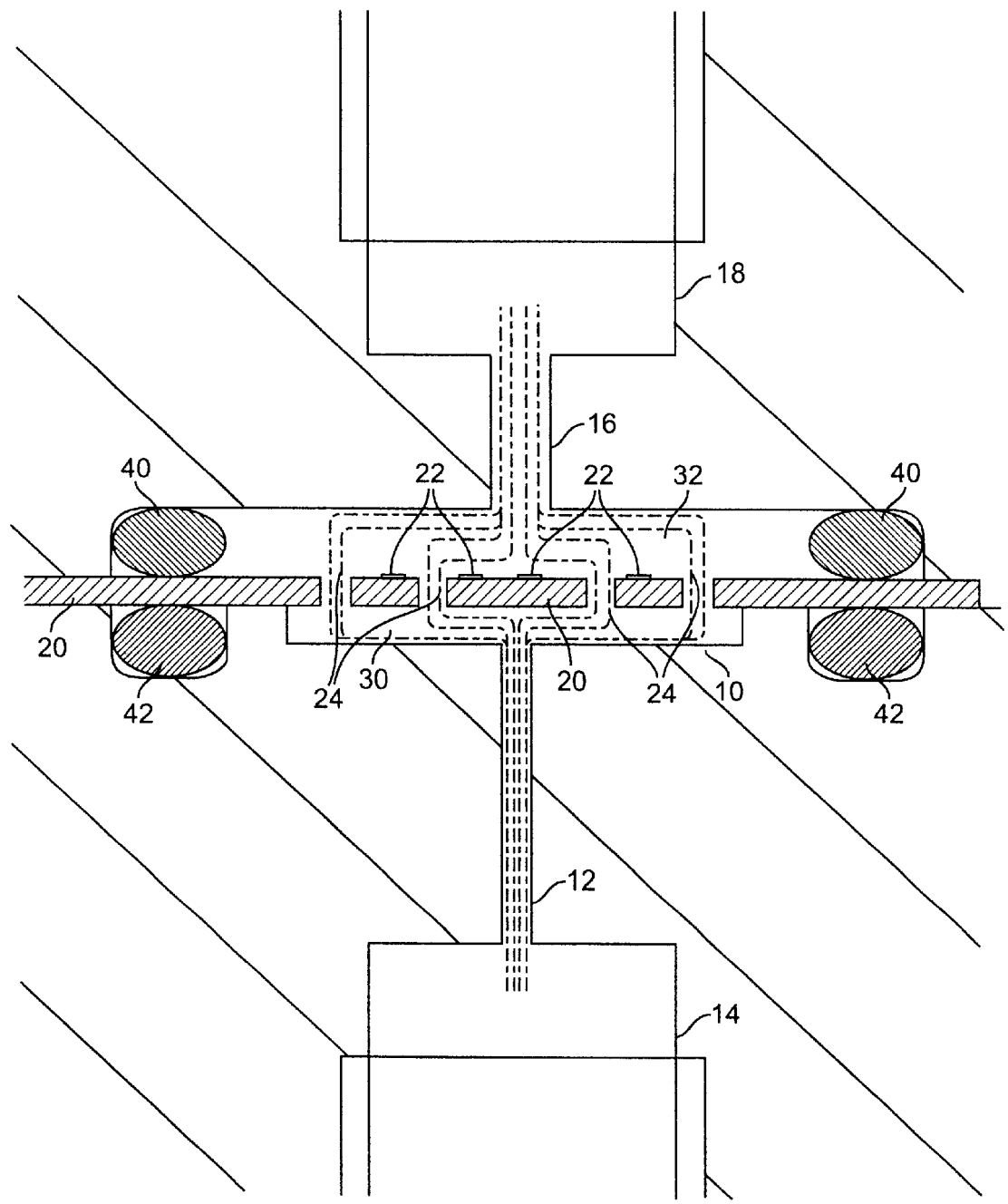

The invention concerns an analytical flow cell with a planar film sensor comprising a cell volume in contact with the film sensor, an input line to this cell volume and the sensor, and an output line for through-flow of a fluid medium to be analyzed. The invention further concerns a film sensor for such an analytical flow cell.

Analytical flow cells with film sensors, especially with thin-film electrodes, are known, and are commonly used now in, for example, gas chromatography or HPLC detectors. Film sensors are also often particularly suitable for miniaturization, and so are suitable for use in miniaturized analytical systems (e. g., "lab-on-a-chip" systems). Here, a detector is considered to be a unit of the actual analytical cell with the sensor and an electronic measuring unit, such as a potentiostat and a signal amplifier. Use of thin film sensors or thin film electrodes in the analytical cell has provided significant advantages for analytical technology. It makes further miniaturization possible, and can make a substantial saving in sensor material. That has led to decidedly more economical measurement cells when the electrode materials are expensive, such as platinum or gold. Thin-film sensors have film thicknesses in the range of nanometers to micrometers. Thick-film sensors with film thicknesses in the micrometer range are being used for certain purposes.

The printed 3-electrode pattern is currently the standard for electrochemical thin-film cells. In such cells the working electrode, reference electrode and auxiliary electrode are printed, with quite varied patterns, and contacts are applied to a carrier. The thin-film or thick-film electrode pattern can also be produced in other manners. Various processes are available for that.

The analytical, or measurement cell, also called a thin-film cell, comprises a cell volume on the electrode side of the carrier, past the electrode, to hold the fluid medium to be analyzed, such as a liquid in HPLC or gas in GC, as well as an inlet and an outlet allowing the medium to flow through, so that the cell is made as a flow cell. Cell volumes are currently generally from one to a few microliters. Cell volumes in the nanoliter region are possible today.

Aside from various electrode geometries, quite varied cell patterns have already been tested and used to attain the best possible flow properties and high sensitivity with the best possible resolution. Dead volumes should be avoided. In one of the cell patterns now in use, the medium being analyzed, i. e., the mobile phase, the mobile phase is directed obliquely in a jet onto the thin film, and removed obliquely again on the opposite side. Another possibility is that of directing the medium being investigated perpendicularly onto the electrode, as much as possible at a point, and removing it at the sides.

In examination of liquids, another problem arises because gases dissolved in the liquid can separate easily at solid surfaces, forming small gas bubbles on the electrode or electrodes during operation. That causes signal distortion and impairs the measurement.

The objective of the invention is to design an analytical flow cell of the type stated initially, and a corresponding film sensor, so as to attain high sensitivity with good resolution even at small cell volumes and, in particular, to avoid formation of bubbles by separation of gases from the liquid being examined at the electrodes or, generally, at the sensor.

To reach this objective, the invention provides for an analytical flow cell with a planar sensor in contact with the cell volume, and an inlet to this cell volume and to the sensor, and an outlet to allow fluid flow, that the sensor has at least one defined passage transverse to the sensor film for fluid medium being analyzed so that the input and outlet are on opposite sides of the film.

The accompanying film sensor for the analysis flow cell according to the invention is correspondingly characterized by the fact that the sensor has at least one defined passage transverse to the sensor film for the passage of a fluid medium to be analyzed.

A "defined passage" in the terminology used in this application, is an opening adapted to the cell geometry, which forms a short channel through the sensor film, transverse to the film, and, optionally, through an underlying carrier.

It was found, surprisingly, that substantial advantages for measurement technology appear if the fluid medium being analyzed is conducted "through the electrode toward the back". Because of the thinness of a film sensor, contact times are short, so that resolution is good. The fluid medium can be moved through the cell by pressure or suction. That also allows potential technological variations not possible with other cell geometries. The amount of gas bubbles forming on the film sensor is distinctly reduced. The new geometry also makes it possible to keep the active cell volume of the flow cell considerably smaller and to avoid dead volumes for the most part.

The cell volume can be adapted to the type of measurement to be done. For instance, the cell volume on the sensor, which makes contact possible between the fluid medium and the sensor, can be designed approximately cylindrical with the axis of the cylinder perpendicular to the sensor film; or it can have approximately conical geometry, with the base of the cone adjacent to the sensitive surface of the film sensor and the tip of the one opening into the inlet. Various cell volumes, larger or smaller in the general range of a few nanoliters up to about 50 microliters, can be produced. There can also be a collecting volume acting as a buffer volume for the fluid medium directly behind the sensor.

The measurement can optionally be multiplied in the form of several parallel or series measurements by use of multiple inputs and outlets and several electrodes.

The analytical flow cell can also advantageously be integrated into a holder which combines all the components of the cell. The holder comprises connections for input and output of the medium being analyzed, and for conducting the signals obtained with the sensor to a detector unit. The holder also comprises means to pick off signals from the sensor which are preferably conducted to a plug as a connector, from which they can be taken off with the usual connecting means, as well as means for separably mounting the sensor in a position in contact with the cell volume.

For the latter, the holder can comprise at least parts separably connected, between which the sensor is placed or mounted in a combination held together by its shape, or clamped. The two separably connected parts can advantageously be connected with a joint or a clamp so that the holder with at least 2 parts can be unfolded. That makes it possible to change the film sensor, which is printed on a carrier with the contacts, in a particularly simple manner. Alternatively, the sensor can be solidly integrated in a unit so that it is not replaceable but is instead firmly combined with the analysis unit, i.e., the microsystem. For instance, it can be completely welded all around, between films, for instance.

The holder can be made of metal or plastic or other suitable material such as ceramic. In one preferred embodiment, the entire cell geometry with the cell volume, collecting volume optionally placed behind the sensor, inputs, outlets, feed and return connections, is integrally formed in this holder. That is, for instance, it is milled from the holder material, or combined into a fluidic part placed in the holder.

Other preferred embodiments are those in which the film sensor is not replaceable, but instead is integrated into a miniaturized analytical system ("microsystem") such as a "lab-on-a-chip" system. Then, for example, the sensor can be heat-sealed inside a microsystem, as stated above. "Lab-on-a-chip" is the term for miniaturized analytical systems. They are also called μTAS, "micro total analysis systems". Advances in microtechnology and progress in integration of microelectronic circuits will in the near future provide complete analytical stations in extremely small spaces which may be of postage stamp size, for instance. These "laboratories" on a chip can be made with mass production processes from the semiconductor, plastics, and printing industries. Thus they are optimally suited as disposable systems in the mass markets of the life sciences (health, nutrition, environment) to improve our quality of life.

Thus the film sensor can be integrated into an analytical station assembled as a unit, which contains other components, such as a pump to supply the liquids being examined, as well as channels in which the purified or chemically converted fluid flows.

As such a system must be very small, and must be produced very economically, it will, among other things, not have any replaceable parts. The film sensor according to the invention is therefore preferably solidly integrated into the flow channel system (for instance, printed onto a plastic part which simultaneously contains the channel).

The film sensor itself which, according to the invention, has at least one defined passage for flow or a fluid medium being analyzed, transverse to the film, can comprise at least one electrode. Preferably, the sensor comprises a multielectrode pattern printed on a carrier, generally with a working electrode, a reference electrode, and an auxiliary electrode, with at least one of the electrodes having a defined passage transverse to the film. The actual sensitive film, i.e., the thin conductive electrode layer printed onto the carrier can be in the immediate vicinity of the passages, immediately adjacent to them, extending into them, or passing through them, so that the passage or passages always run effectively transverse to the electrode, i.e., to the sensor layer. The electrodes need not all be printed on the same side of the carrier. For example, the working electrode can be in front of the carrier in the direction of flow, with the reference and auxiliary electrodes placed after the carrier in the direction of flow. The film sensor is preferably a thin film sensor.

The sensor can also be a biosensor, preferably comprising a thin film fixed onto a carrier. This thin film can, for instance, be platinum, gold, or graphite, and can be coated with enzymes or other biomaterials such as antibodies.

In general, the sensor can be a biosensor or a chemosensor, such as an ion-selective electrode, a pH electrode, or another electrode. Electrochemical measurements can be done as usual, for instance, potentiometrically, amperometrically, or polarographically.

According to the invention, at least one passage is provided in the sensor or in the electrode. However, there can also be multiple passages with different geometries, so that when multiple electrodes are used there can be one or more passages in various electrodes.

The passages can be in the sensitive layer itself as well as in the immediate vicinity, that is, directly on the layer or adjacent in the same plane, such as in the carrier. In the case of a sensitive layer of carrier and coating, then, the sensitive layer can be immediately beside the passages, which are in any case placed transverse to the entire sensor film, adjacent to them, projecting into them, or passing through them.

The passages are preferably round and of constant diameter through the film thickness. The passages can, though, be arranged transverse to the film conically or in some other suitable geometry.

The invention is explained in more detail in the following by means of the example embodiments in the drawing.

The drawings show:

FIG. 1: A cell with 4 passages through a multielectrode pattern printed on a carrier.

Figure 2A:
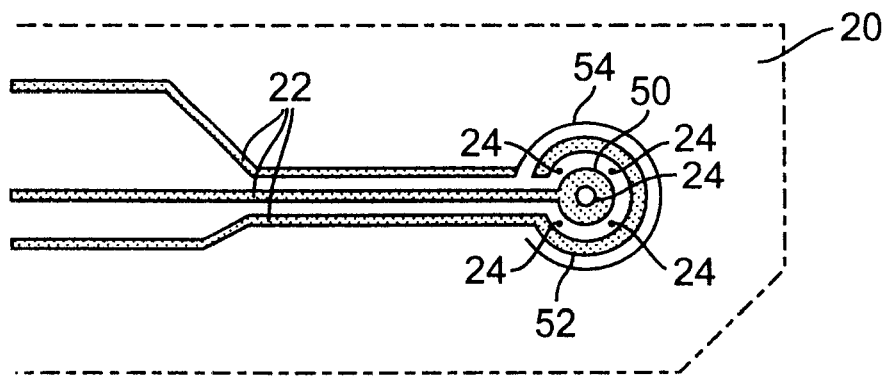
Figure 2B:
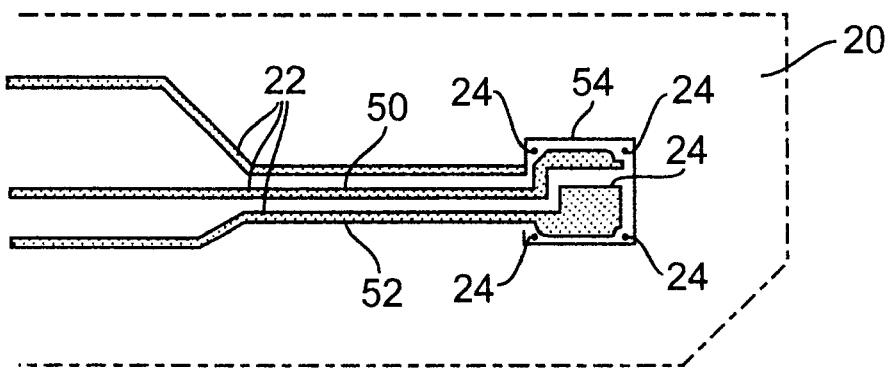
Figure 2C:
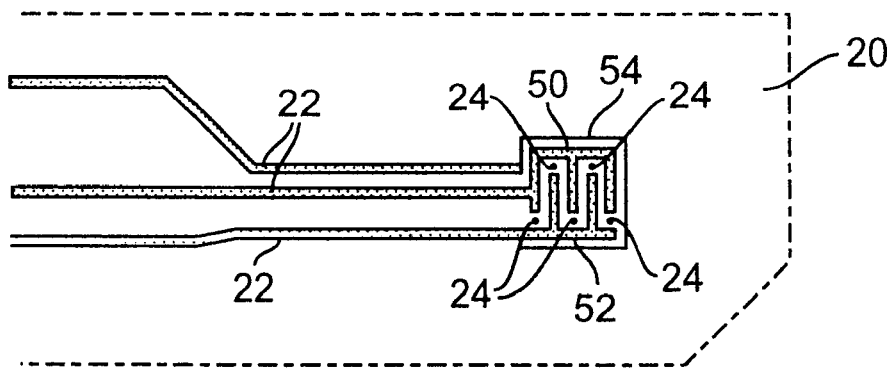
Figure 3A:
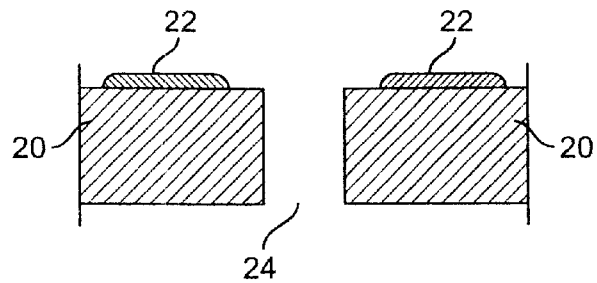
Figure 3B:
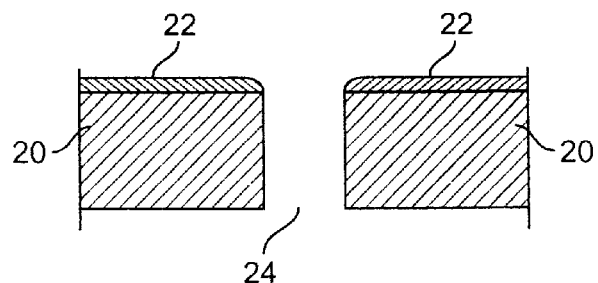
Figure 3C:
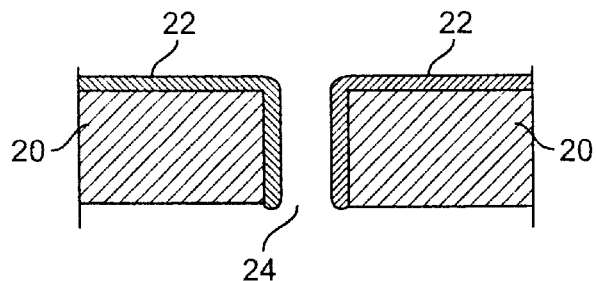
Figure 3D:
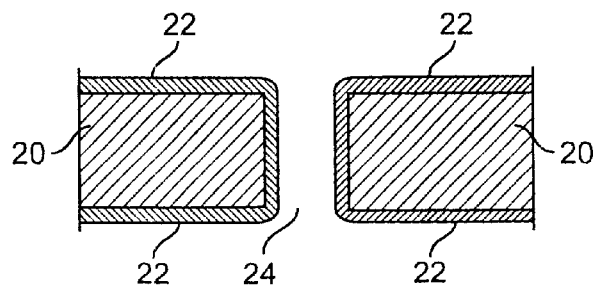

FIG. 2: Various 3-electrode geometries, each with multiple passages in different arrangements.

FIG. 3: Various geometries with respect to the passages with a film sensor comprising a carrier and a sensitive coating.

Figure 4:
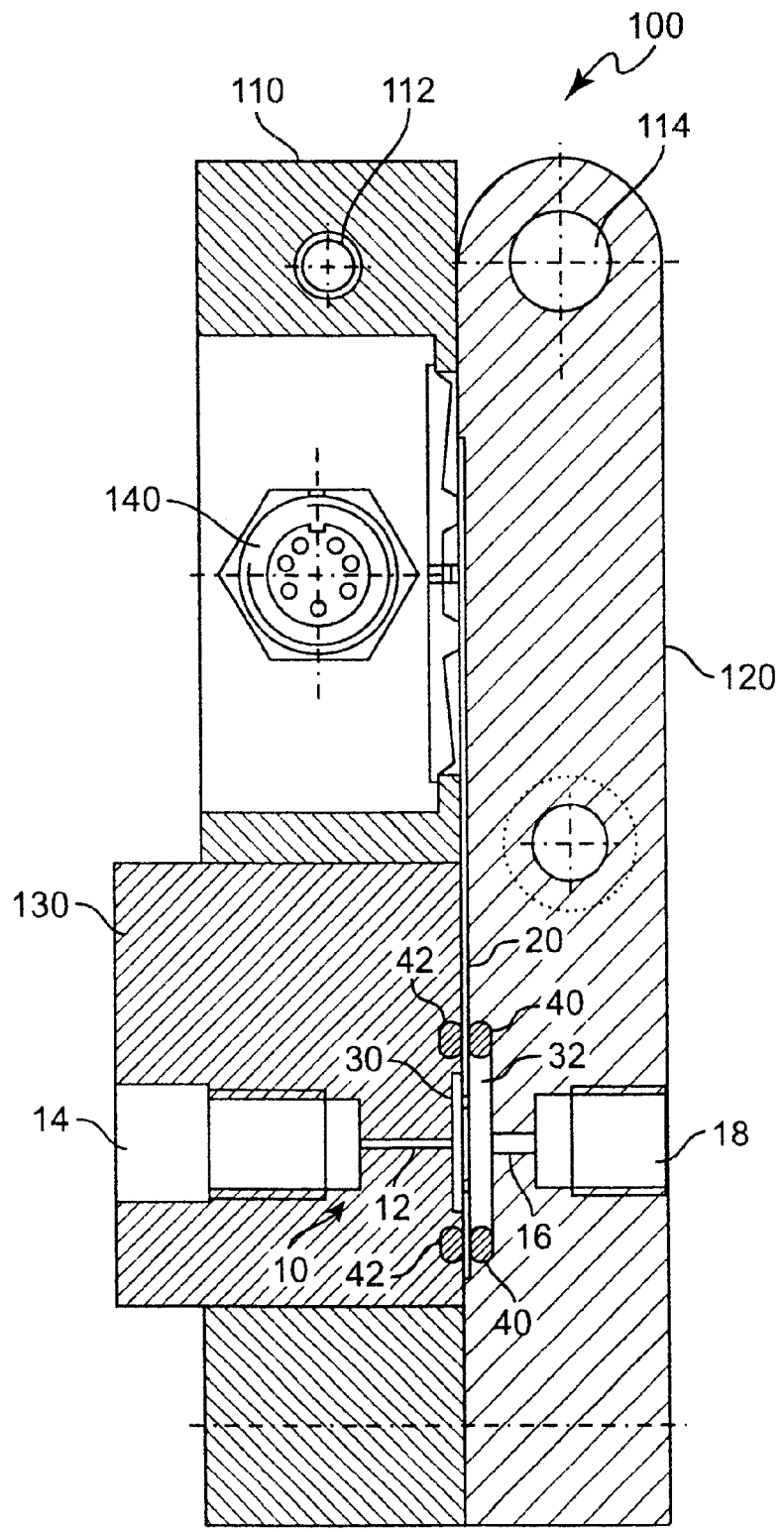
Figure 5A:
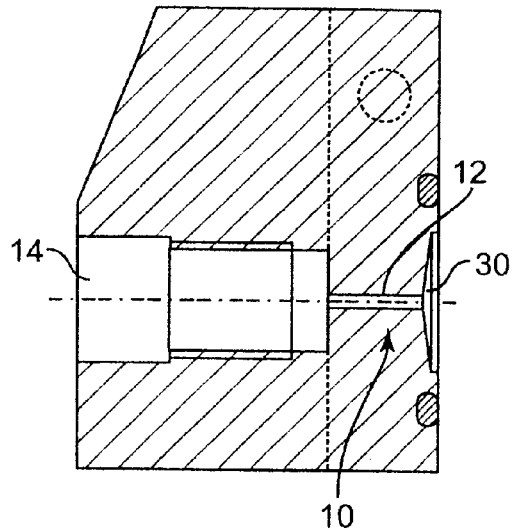
Figure 5B:
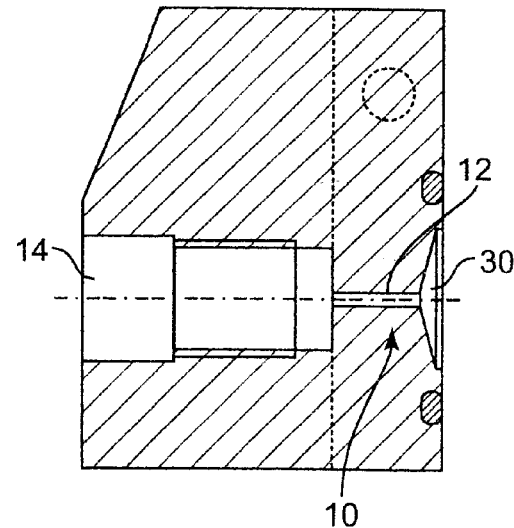
Figure 5C:
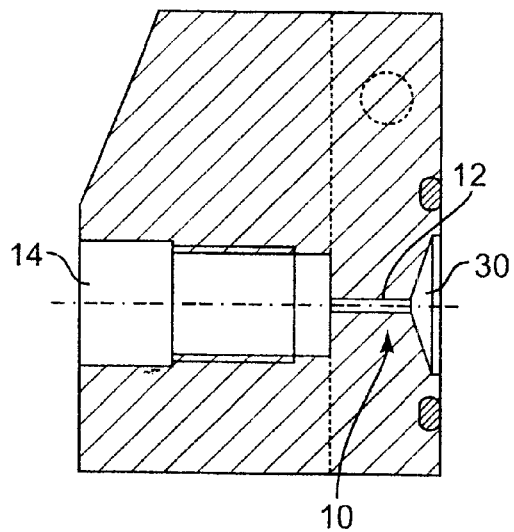
Figure 5D:
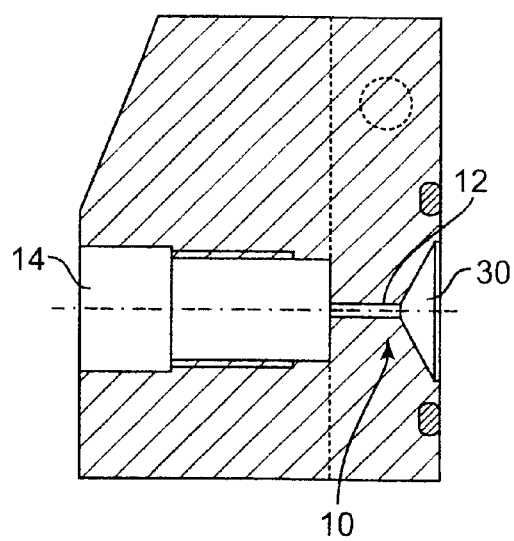

FIG. 4: A holder made up of 2 parts connected by a joint, and an additional replaceable fluidic part.

FIG. 5: Four different fluidic parts differing in the cone angle of the conical cell volume.

Figure 6:
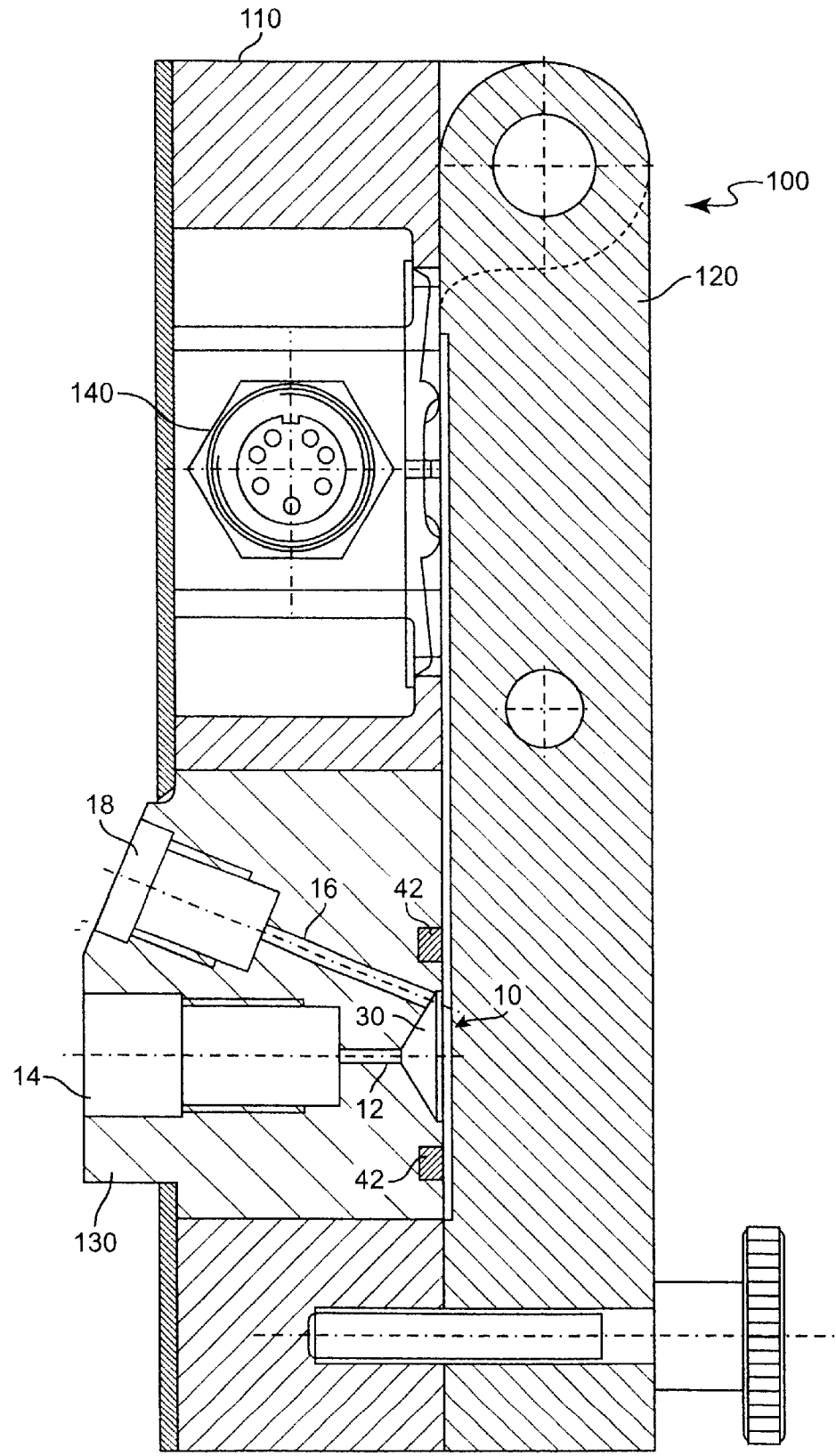

FIG. 6: A holder corresponding to FIG. 4, but with the usual cell geometry.

FIG. 1 shows a cell 10, integrated into, or milled out of, the material of a holder which is not shown in its entirety, with an input 12 and an input connection 14 as well as an outlet 16 on the opposite side of the cell and its outlet connection 18 leading to the outside. The intake side with input 12 and the outlet side with its outlet 16 are placed in two separate, separably connected parts of the holder between which is the sensor 20. The sensor 20 comprises a carrier with a 3-electrode pattern 22 of working electrode, auxiliary electrode and reference electrode printed on one side. A cell volume 30 is shown above those electrodes on the inlet side. It accepts the fluid medium flowing out of the inlet 12 and distributes that medium over the electrode surfaces. In this example, sensor 20 has four passages 24 through which the fluid medium flows into a collecting volume 32 behind the sensor and is carried away from the cell through the outlet connection 16. The volumes 30 and 32 are sealed off from the replaceably inserted sensor 20 by the O-rings 40 and 42. The cell geometry shown allows flow, free of directional changes and, therefore, free of disturbing turbulences, into the flow cell. The fluid can be moved through the cell by pressure or suction. Bubble formation in the electrode region 22 can be prevented.

FIG. 2 shows various 3-electrode geometries, each with multiple passages 24 in different arrangements, 1) with 4 passages 24 arranged evenly around the periphery of a circular working electrode 50 in the carrier, with the central electrode 50 having another central passage 24, and with that electrode surrounded concentrically by annual auxiliary and reference electrodes (52, 54);

2) with 4 passages 24 at the corners and one central passage 24 in a pattern with a square periphery; and 3) with 5 passages 24 adjacent to the endpoints of two electrodes (52, 54) which interpenetrate in the form of combs.

These geometries must be understood as examples. Many other geometries are conceivable. In the examples shown here, some of the passages 24 are adjacent to the thin electrode film printed in the carrier, and part are in the thin electrode film.

FIG. 3 shows various geometries with respect to the passages 24 for a film sensor 20 comprising carrier and sensitive coating 22. The flow cell is not shown here, only the substrate plate (carrier) on which the sensitive film 22 is placed. The following specific geometries are shown:
1) The electrode film is on the substrate beside the passage.
2) The electrode film extends to the edge of the passage.
3) The electrode film extends into the passage.
4) The electrode film covers the front and back.

FIG. 4 shows a holder, designated as 100, which is not shown in its entirely, made up of 2 parts (110, 120) which are clamped together by the holes 112 and 114. The actual flow cell 10 has the geometry shown in FIG. 1, and identical reference numbers indicate identical components. The fluidic part 130 is inserted into the holder 100 as a block comprising the intake-side components of the cell 10, so that different cell volumes can be used (by exchanging them). Contacts on the sensor 20 are connected externally at the boundary layer to sensor 20 so that the signals produced are taken off and can be taken off through a plug 140 on the outside of the holder.

FIG. 5 shows four different fluidic parts 130, such as can be used in the holder 100 shown in FIG. 4. Variation of the cone angle a) 10°, b) 15°, c) 20°, d) 30° defines various volumes which increase the order shown. The different fluidic parts are used depending on the purpose of the analysis.

FIG. 6, finally, shows a holder corresponding to FIG. 4 but with the usual cell geometry in the fluidic part 130. The input and output here are through the fluidic part 130, corresponding to the state of the art [at the time of] the application. Even here, the arrangement with the 2 foldable holder parts (110 and 120) which make simple exchange of the sensor 20 possible is advantageous.

What is claimed is:

1. Analytical flow cell, comprising:
   a planar sensor;
   a cell having a cell volume in contact with the sensor, said cell volume having an inlet and an outlet to allow flow of a fluid medium to be analyzed; and
   wherein the sensor has at least one defined passage that is of constant diameter transverse to the sensor for a flow medium to be analyzed, with said inlet and said output on opposite sides of the sensor.

2. The analytical flow cell according to claim 1, wherein the cell volume is made of approximately conical shape with the base of the conical shape adjacent to a sensitive area of the sensor.

3. The analytical flow cell according to claim 1 or 2, further comprising a collecting volume on an outlet side of the cell volume directly behind the sensor.

4. The analytical flow cell according to claim 3, wherein said input is comprised of multiple inlets and said output is comprised of multiple outlets.

5. The analytical flow cell according to claim 3, further comprising a holder which holds connectors for input and removal of the flow medium to be analyzed and for taking off signals obtained with the sensor to a detector unit, wherein the cell is placed within the holder, and the holder having
   means to obtain signals from the sensor and
   means for separably mounting the sensor in a position in contact with the cell volume.

6. The analytical flow cell according to claim 5, wherein the holder is made up of at least two parts separably connected together, between which the sensor is placed.

7. The analytical flow cell according to claim 6, wherein the holder is made up of said at least two parts that can be unfolded.

8. The analytical flow cell according to claim 5, wherein the holder is of metal or plastic, and wherein the cell has a geometry that is made so that it is integrated into the holder or into a replaceable fluidic part in the holder.

9. An analytical flowcell comprising a film sensor that is a biosensor or an ion-selective electrode and has at least one defined passage that is of constant diameter so that a fluid medium to be analyzed can flow through it transverse to the film.

10. The analytical flowcell according to claim 9, wherein the sensor is an ion-selective electrode.

11. The analytical flowcell according to claim 9, wherein the sensor is a biosensor or an ion-selective electrode comprising a thin film fixed onto a carrier.

12. The analytical flowcell according to claim 11, wherein the at least one defined passage is formed in the thin film or immediately adjacent to the thin film in the carrier.

13. The analytical flowcell according to claim 9, wherein the at least one defined passage has a circular cross section.

14. The analytical flowcell according to claim 9, wherein the sensor comprises a multielectrode pattern printed on a carrier with at least one electrode having at least one defined passage of constant diameter transverse to the film.

15. The analytical flowcell according to claim 14 or 11, wherein a sensitive film of the sensor applied to a carrier is in the immediate vicinity of the at least one defined passage, adjacent to the at least one defined passage, projecting into the at least one defined passage, or passing through the at least one defined passage.

16. The analytical flowcell according to claim 15, wherein the sensor is constructed in a manner which allows measuring glucose, alcohol, lactate, glutamine, glutamate, sulfite, or hydrogen peroxide.

* * * * *